United States Patent
Knecht

(10) Patent No.: US 10,034,789 B2
(45) Date of Patent: Jul. 31, 2018

(54) DYNAMIC FORCE HINGE JOINT FOR KNEE BRACE AND KNEE BRACE EQUIPPED THEREWITH

(71) Applicant: Townsend Industries, Inc., Bakersfield, CA (US)

(72) Inventor: Steven S. Knecht, Gardnerville, NV (US)

(73) Assignee: Townsend Industries, Inc., Bakersfield, CA (US)

( * ) Notice: Subject to any disclaimer, the term of this patent is extended or adjusted under 35 U.S.C. 154(b) by 385 days.

(21) Appl. No.: 14/772,142

(22) PCT Filed: Feb. 20, 2014

(86) PCT No.: PCT/US2014/017263
§ 371 (c)(1),
(2) Date: Sep. 2, 2015

(87) PCT Pub. No.: WO2014/143518
PCT Pub. Date: Sep. 18, 2014

(65) Prior Publication Data
US 2016/0015546 A1    Jan. 21, 2016

Related U.S. Application Data

(60) Provisional application No. 61/792,099, filed on Mar. 15, 2013.

(51) Int. Cl.
*A61F 5/01* (2006.01)
*A61F 5/30* (2006.01)

(52) U.S. Cl.
CPC .......... *A61F 5/0125* (2013.01); *A61F 5/0123* (2013.01); *A61F 5/30* (2013.01)

(58) Field of Classification Search
CPC ........ A61F 5/0125; A61F 5/0123; A61F 5/30; A61F 2005/0139; A61F 5/0102; A61F 2005/0167
See application file for complete search history.

(56) References Cited

U.S. PATENT DOCUMENTS

| 3,826,251 | A | 7/1974 | Ross |
| 6,413,232 | B1 | 7/2002 | Townsend et al. |
| 2004/0267179 | A1 | 12/2004 | Lerman |
| 2005/0192523 | A1 | 9/2005 | Knecht et al. |

(Continued)

FOREIGN PATENT DOCUMENTS

| CN | 1662194 A | 8/2005 |
| CN | 101404961 A | 4/2009 |

(Continued)

*Primary Examiner* — Ophelia A Hawthorne
(74) *Attorney, Agent, or Firm* — David S. Safran

(57) ABSTRACT

A hinge joint for orthopedic knee braces that enable a wearer or medical professional to quickly and efficiently adjust the lateral corrective force placed on the knee joint so as to apply the force at heel strike (full extension) when it is most needed, but will relax the loading during flexion. The hinge joint, for use in a three point pressure system of a knee brace, has a first part that is connectable to a femoral arm of a knee brace and a second part that is mounted to be able to telescope out of the first part as the leg is extended and to telescope back into the first part as the leg flexes.

4 Claims, 6 Drawing Sheets

(56) References Cited

U.S. PATENT DOCUMENTS

2006/0241540 A1 10/2006 Doty et al.
2012/0143111 A1* 6/2012 Bledsoe ................ A61F 5/0123
602/26

FOREIGN PATENT DOCUMENTS

| CN | 202740170 U | 2/2013 |
| EP | 0 615 734 A1 | 9/1994 |
| WO | 2011/163667 A1 | 12/2011 |
| WO | 2012/075148 A2 | 6/2012 |

* cited by examiner

A)

B)

C)

D)

A)

B)

C)

D)

DYNAMIC FORCE HINGE JOINT FOR KNEE BRACE AND KNEE BRACE EQUIPPED THEREWITH

CROSS REFERENCE TO RELATED APPLICATION

This application is a § 371 of International Application No. PCT/US2014/017263, filed Feb. 20, 2014 and non-provisional conversion of provisional application 61/792,099.

BACKGROUND OF THE INVENTION

Field of the Invention

The present invention is directed to hinge joints for orthopedic knee braces, particularly for braces that enable a wearer or medical professional to quickly and efficiently adjust the lateral corrective force placed on the knee joint.

Description of Related Art

A knee brace of the type for which the hinge joint of the present application is intended is disclosed in U.S. Pat. No. 6,413,232. Correction of the lateral corrective force placed on the knee joint via a three point pressure system is obtained in this brace by the provision of a spring-loaded ratchet mechanism that features a series of interlocking teeth that allows for the horizontal displacement of the condyle pad support. However, this is a static device that once adjusted, is the same at all angles of flexion. As a result, this joint increases the medial/lateral displacement throughout the range of motion.

Similarly, in the knee brace of U.S. Pat. No. 6,981,957, which utilizes a pair of hinges, one of which provides for movement in a posterior-anterior plane and the other which provides for movement in a medial-lateral plane, pressure is always applied even when sitting down.

SUMMARY OF THE INVENTION

Therefore, it is a primary object of the present invention to provide a joint for orthopedic knee braces that enable a wearer or medical professional to quickly and efficiently adjust the lateral corrective force placed on the knee joint so as to apply the force at heel strike (full extension) when it is most needed, but will relax the loading during flexion.

This object is achieved by providing a joint that can add correction to a three point pressure system of a knee brace by telescoping the condyle out as the leg is extended and in as the leg flexes. According to a preferred form of the joint, the joint is formed of a condyle cam part and condyle driver part which are move relative to each other as leg flexes and extends.

DETAILED DESCRIPTION OF THE INVENTION

Figure 1:
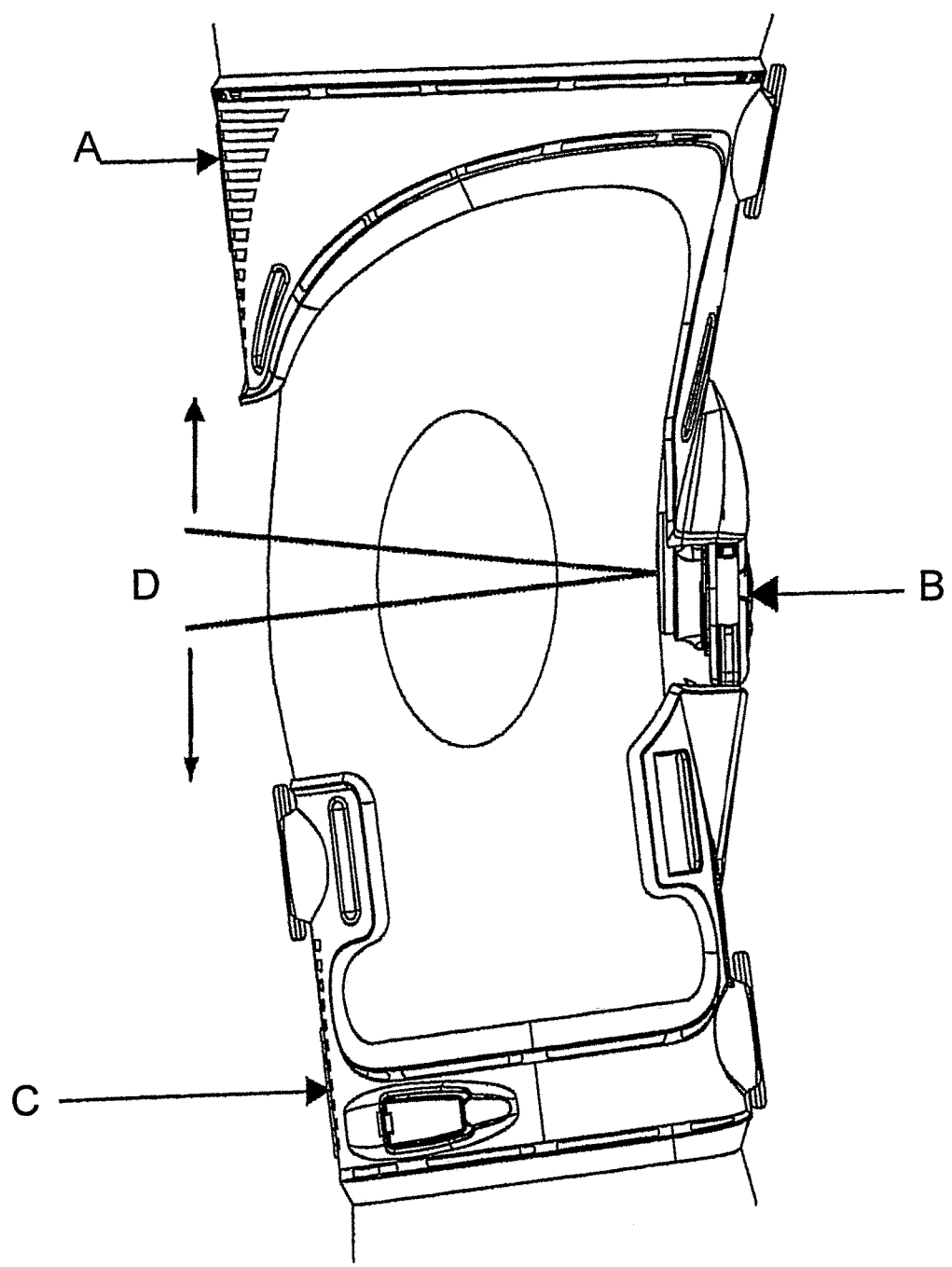
FIG. 1 schematically shows a knee brace equipped with the joint of the present invention on the leg of a user.

FIG. 1 shows a knee brace equipped with a joint according to the present invention for purposes of illustrating the three point pressure system adjusted by the joint of the present invention. As is shown, two force points A, C are created at the medial (interior) side of the leg by femoral and tibial crosspieces or straps with a third force point B occurring at the lateral side joint which acts on the lateral condyle of the knee. Increasing and decreasing loading at the lateral condyle changes the angulation of the leg with the goal of minimizing the pressure on the compromised compartment of the leg D during full extension/heel strike.

Figure 2:
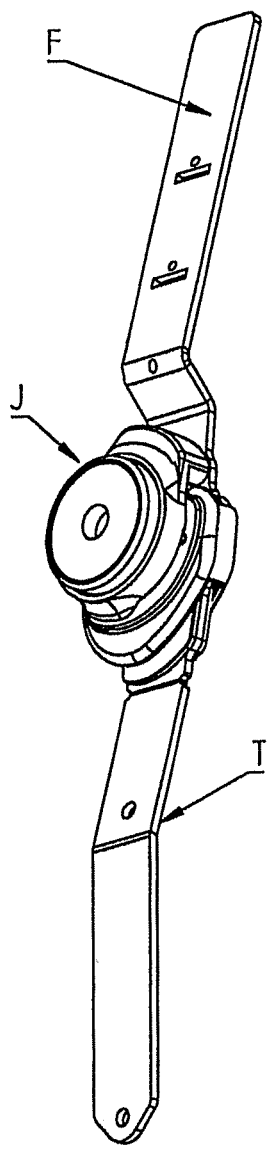
FIGS. 2 & 3 are, respectively, inner side and outer side perspective views of the joint of the present invention connecting a tibial arm of a knee brace to a femoral arm of a knee brace.
Figure 3:
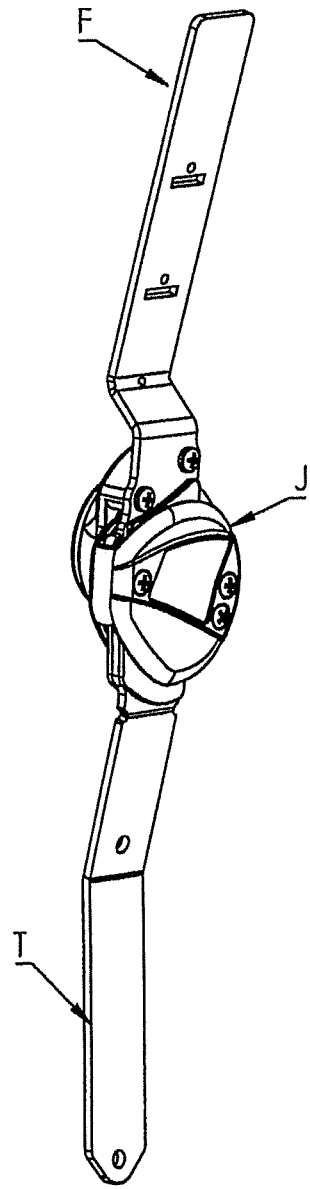
Figure 5:
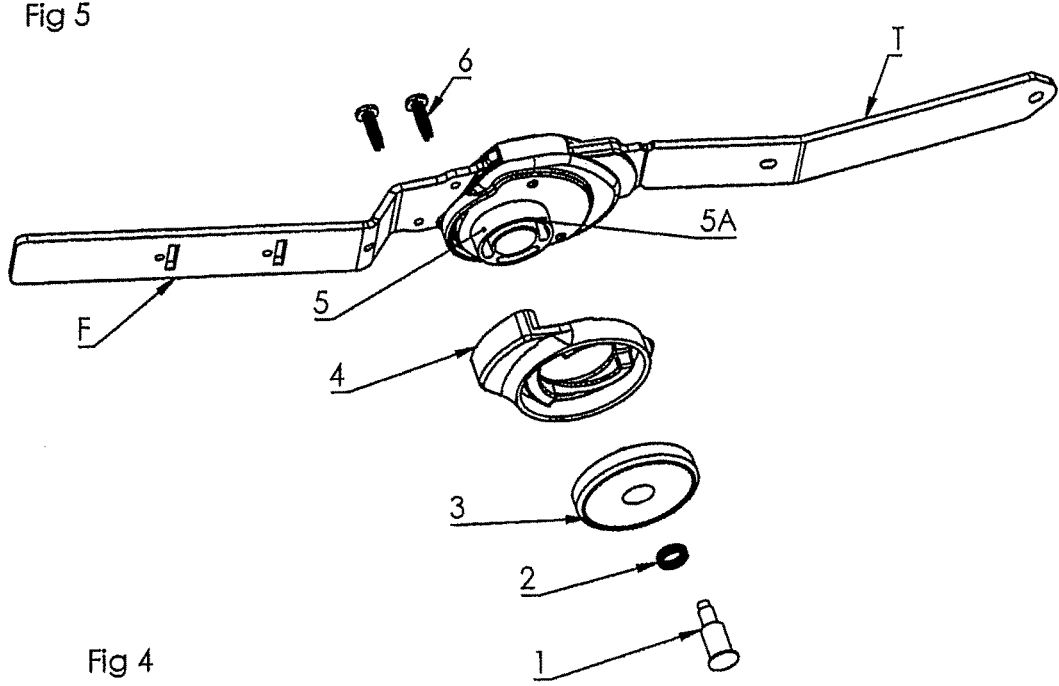
FIGS. 4 & 5 are exploded perspective views of joint of the present invention connecting a tibial arm of a knee brace to a femoral arm of a knee brace as seen from the outer and inner sides thereof, respectively.
Figure 4:
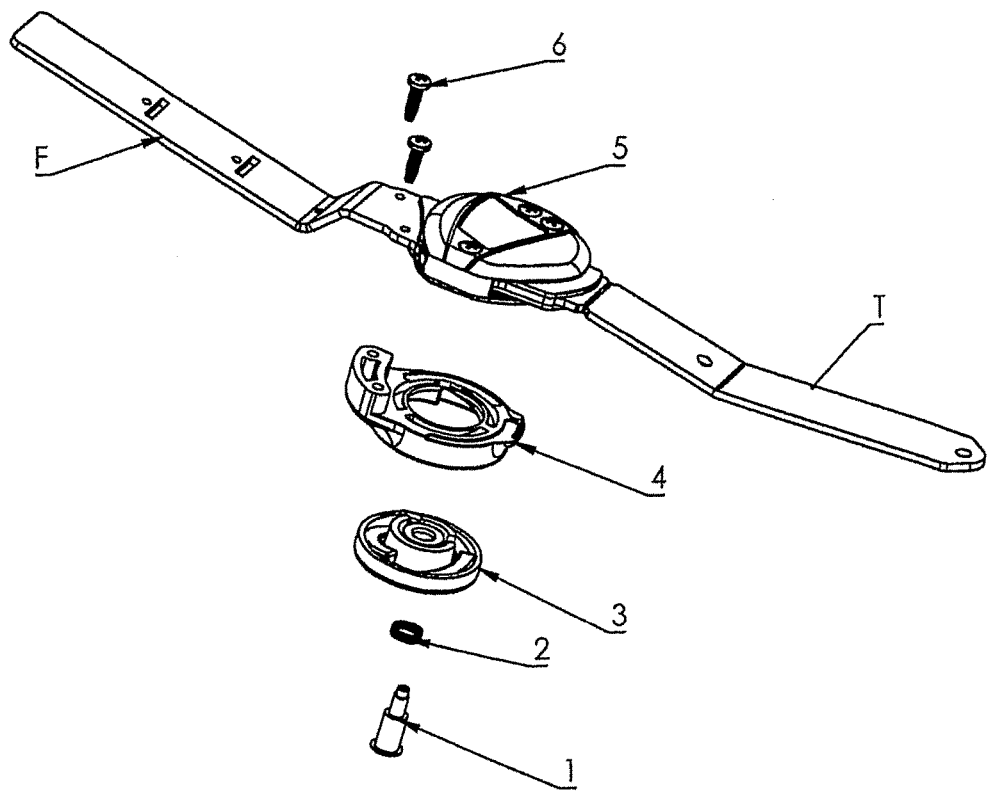
Figure 6:
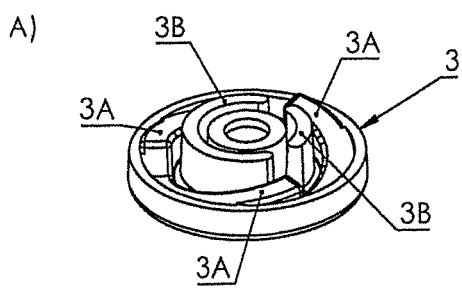
FIGS. 6A-D & 7A-D are, respectively, interior perspective, interior elevational, side elevational, and exterior elevational views of the condyle cam and condyle driver of the present invention.
Figure 6:
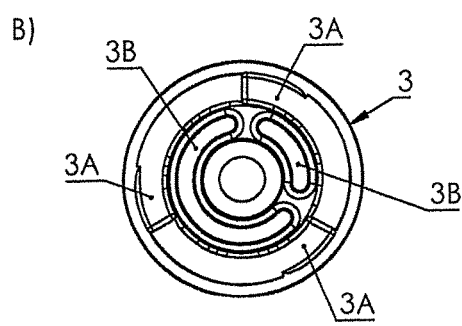
Figure 6:
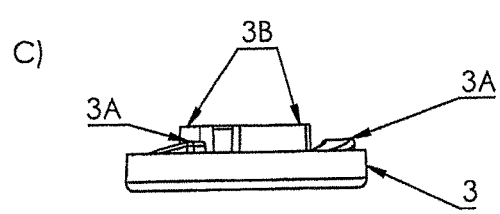
Figure 6:
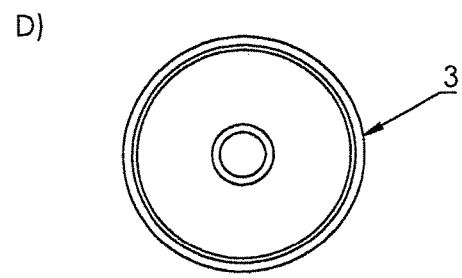
Figure 7:
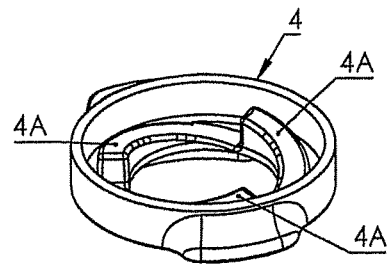
Figure 7:
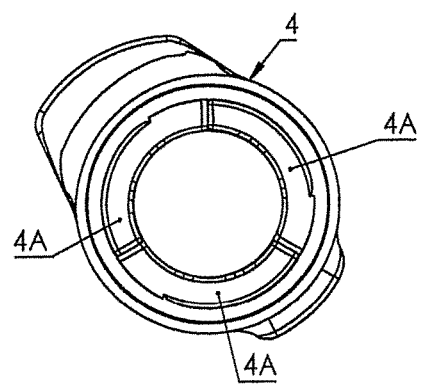
Figure 7:
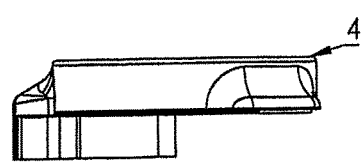
Figure 7:
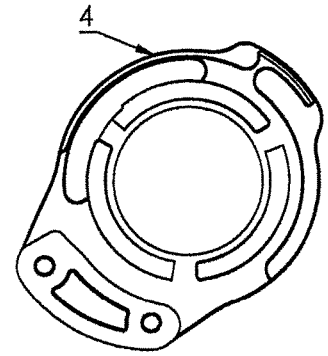
Figure 8:
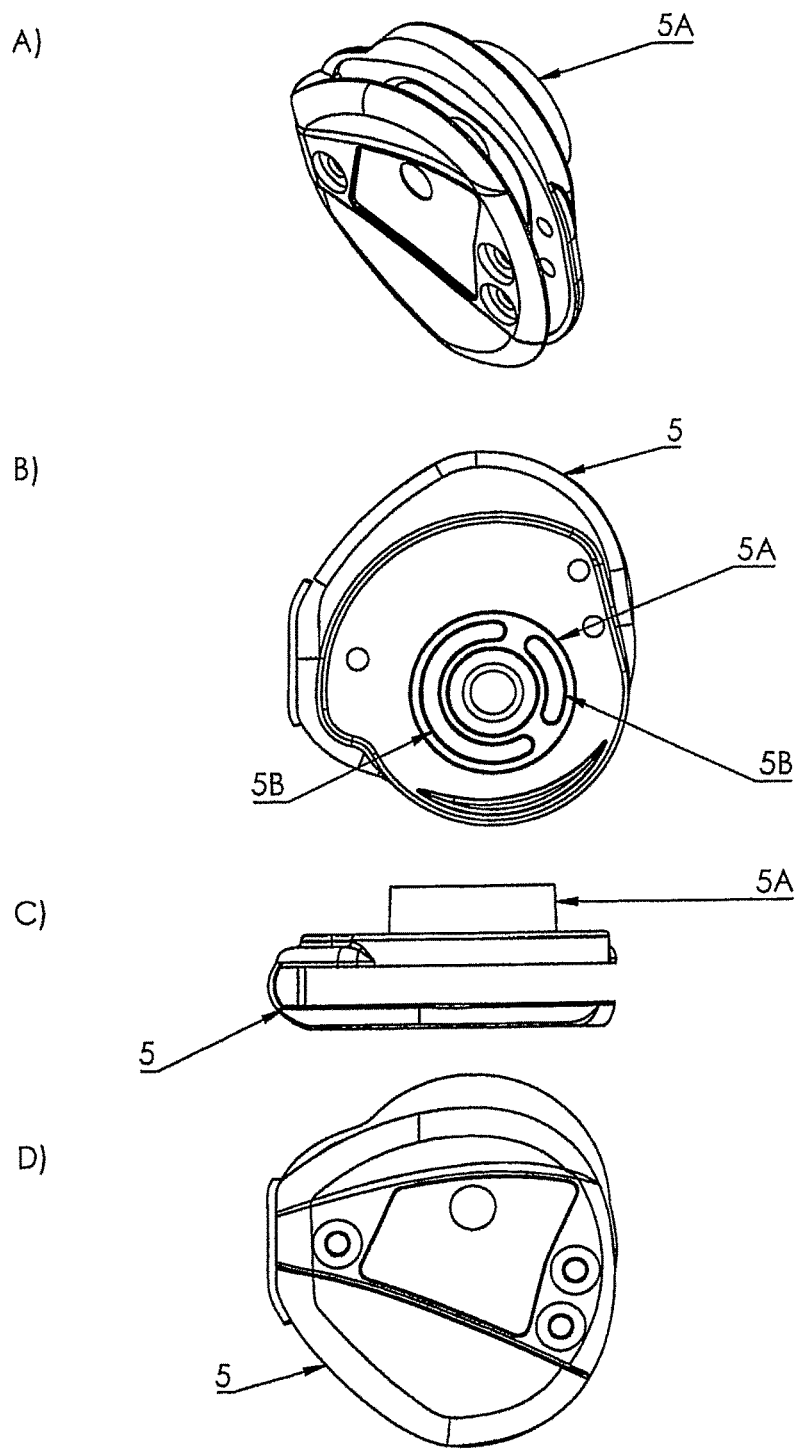
FIGS. 8A-D are, respectively, interior perspective, interior elevational, side elevational, and exterior elevational views of the hinge cap of the joint of the present invention.

FIGS. 2 & 3 show the inventive joint J connecting a femoral arm F to a Tibial arm T of the knee brace shown in FIG. 1. As can be seen from FIGS. 4-8, the hinge joint of the present invention is comprised of a rivet 1, a return spring 2, a condyle cam 3, a condyle cam driver 4, a hinge cap 5 and attaching screws 6. The interior of condyle cam 3 and a condyle cam, driver 4 face each other and are provided with ramps 3a, 4a respectively.

The condyle cam driver 4 is attached to the femoral arm F with two screws 6 and rotates around the center boss 5a on the hinge cap 5. During extension of the hinge joint J, the condyle cam driver 4 rotates with the femoral arm F of the joint J. As condyle cam driver 4 rotates the three ramps 4a slide against the opposing ramps 3a on the condyle cam 3. This movement of the ramps over each other forces the condyle cam 3 to extend (project) against the lateral side of the knee condyle while compressing the return spring 2. Rotation of condyle cam 3 is prevented by the two protrusions 3b that engage into complementarily shaped slots 5b in the hinge cap 5.

During flexion of the joint J, the return spring 2 forces condyle cam 3 to slide down the ramps 4a in cam driver 4, thereby allowing condyle cam 3 to retract into cam driver 4 with a resultant decreasing of the lateral load on the knee during flexion, being fully retracted at full flexion. On the other hand, at full extension, the condyle cam is fully extended.

Figure 9:
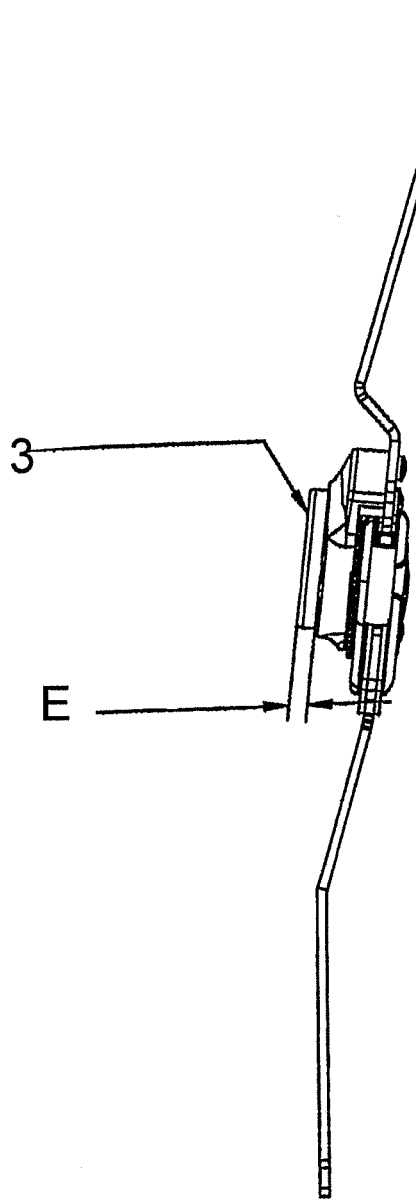
FIGS. 9 & 10 are views of the joint of the present invention connecting a tibial arm of a knee brace to a femoral arm of a knee brace in full extension and full flexion, respectively.
Figure 10:
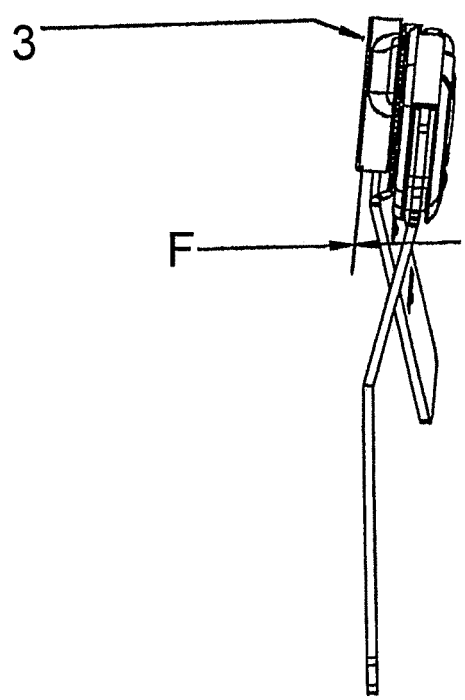

Thus, the hinge joint of the present invention is able dynamically change the pressure applied to the lateral side of the knee condyle with changes in the angulation of the leg so that, at heel strike (or full extension; FIG. 9), the pressure on the compromised compartment of the leg is minimized. That is, the condyle cam applies force at heel strike when it is needed most and relaxes during flexion. Thus, at full extension, the condyle cam is fully extended as shown at E in FIG. 9 while at full flexion, the condyle cam 3 is fully retracted as shown at F in FIG. 10.

It should be appreciated that the brace shown in FIG. 1 is only one of the various types of knee braces that exist and those of ordinary skill will appreciate that the hinge joint the present invention can be incorporated into many other types of braces than that shown. Likewise, while the particular embodiment shown has three ramps 3*a*, 4*a*, other numbers of ramps can be used, the slopes thereof being adjusted accordingly. Similarly, while the particular embodiment shown is contemplated for use as a so-called Townsend motion joint (see, e.g., U.S. Pat. No. 5,259,832), the invention is easily adaptable for use as a geared polycentric or single pivot joint.

What is claimed is:

1. A hinge joint (J) for use in a three point pressure system of a knee brace comprising a first part (4) that is connectable to a femoral arm (F) of a knee brace and a second part (3) that is telescopically mounted to the first part, characterized in that the telescopic mounting of the second part (3) to the first part (4) is constructed in a manner that enables second part (3) to telescope out of the first part (4) as the leg is extended and to telescope back into the first part (4) as the leg flexes so as to dynamically change the pressure applied to the lateral side of the knee condyle with changes in the angulation of the leg.

2. The hinge joint according to claim 1, wherein each of the first (4) and second (3) parts have ramps (3A, 4A), the ramps (3A) of the second part riding over the ramps (4A) of the first part during flexion and extension.

3. A knee brace having three point pressure system, comprising:

a femoral arm (F), a tibial arm (T), and a hinge joint (J) connecting the femoral arm (F) with the tibial arm (T), wherein the hinge joint (J) comprises a first part (4) that is connected to the femoral arm (F) and a second part (3) that is that is telescopically mounted to the first part (4), characterized in that the telescopic mounting of the second part (3) to the first part (4) is constructed in a manner that enables second part (3) to telescope out of the first part (4) as the leg is extended and to telescope back into the first part (4) as the leg flexes so as to dynamically change the pressure applied to the lateral side of the knee condyle with changes in the angulation of the leg.

4. The knee brace according to claim 3, wherein each of the first (4) and second (3) parts have ramps (3A, 4A), the ramps of the second part (3A) riding over the ramps of the first part (4A) during flexion and extension.

* * * * *